United States Patent [19]

Mills et al.

[11] Patent Number: 4,977,264
[45] Date of Patent: Dec. 11, 1990

[54] PROCESS FOR THE PRODUCTION OF 4,5-DICHLORO-6-ETHYLPYRIMIDINE

[75] Inventors: Lester Mills, Naters; Felix Previdoli, Brig, both of Switzerland

[73] Assignee: Lonza Ltd., Gampel/Valais, Switzerland

[21] Appl. No.: 433,134

[22] Filed: Nov. 8, 1989

[30] Foreign Application Priority Data

Nov. 21, 1988 [CH] Switzerland .......................... 4306/88

[51] Int. Cl.$^5$ ........................................... C07D 239/30
[52] U.S. Cl. .................................................... 544/334
[58] Field of Search ......................................... 544/334

[56] References Cited

FOREIGN PATENT DOCUMENTS 0264217 4/1988 European Pat. Off. .
58-222076 12/1983 Japan .

OTHER PUBLICATIONS

"4-Methyl-6-Hydroxypyrimidine", H. M. Foster and H. R. Snyder, Organic Syntheses, Collective vol. 4, pp. 638-640 (1963).

Primary Examiner—John M. Ford
Attorney, Agent, or Firm—Fisher, Christen & Sabol

[57] ABSTRACT

2-chloro-3-oxopentanoic acid alkyl ester is condensed with the addition of bases with formamidinium salts into 5-chloro-6-ethyl-4-hydroxypyrimidine. The latter is converted with phosphoryl chloride into 4,5-dichloro-6-ethylpyrimidine.

6 Claims, No Drawings

1

PROCESS FOR THE PRODUCTION OF 4,5-DICHLORO-6-ETHYLPYRIMIDINE

FIELD OF THE INVENTION

The invention relates to the production of 4,5-dichloro-6-ethylpyrimidine.

BACKGROUND ART 4,5-dichloro-6-ethylpyrimidine is a valuable intermediate product for the production of 4-amino-5-chloro-6-ethylpyrimidines, which exhibit insecticidal, acaricidal and fungicidal properties (European Published Pat. application No. 0264217). Previously known processes for the production of 4,5-dichloro-6-alkyl pyrimidines start from the corresponding 4-hydroxy-6-alkyl pyrimidines, which are first converted with elementary chlorine or a chlorine-carrying agent, such as, N-chlorosuccinimide into the 5-chloro-4-hydroxy-6-alkyl pyrimidines (Japanese Published Pat. application No. 222070/83). The latter is then converted with phosphoryl chloride or another inorganic acid chloride into the 4,5-dichloro compounds. It is true that this process in itself can be performed with good yield and is also suitable for industrial scale application, but the drawback is that the required 4-hydroxy-6-alkyl pyrimidines are only poorly accessible. Their synthesis usually starts from the corresponding 2-thio-6-alkyluracil, which is desulfurized with Raney nickel. It is true that the 2-thio-6-alkyl uracils are easy to produce from the corresponding 3-oxocarboxylic acid esters and thiourea (*H.M. Foster and H.R. Snyder*, Org. Synth., Coll. Vol. IV, 638), but the desulfurization with Raney nickel is not practical for an industrial process.

BROAD DESCRIPTION OF THE INVENTION

The object of the invention is to provide a process for the production of 4,5-dichloro-6-ethylpyrimidine that can be performed economically on an industrial scale.

According to the invention, the object of the invention is achieved by the process wherein a 2-chloro-3-oxopentanoic acid ester of general formula

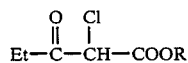  (2)

is first condensed in a polar, protic solvent in the presence of a base with a formamidinium salt of the formula:

  (3)

into 5-chloro-6-ethyl-4-hydroxypyrimidine (4), and the latter is then reacted with phosphoryl chloride in a way known in the art into the target compound.

Suitably there is used, as the 2-chloro-3-oxopentanoic acid ester, a lower alkyl ester, and R is an alkyl group with to 4 C atoms, such as, a methyl, ethyl, propyl, isopropyl, butyl, isobutyl, sec.-butyl or tert.-butyl ester, preferably the methyl or ethyl ester, especially preferably the methyl ester. These esters can be easily obtained from the corresponding 3-oxopentanoic acid esters by chlorination, preferably with sulfuryl chloride. The production of the 3-oxopentanoic acid esters is known from Swiss Published Pat. Document No. 655,301. In a preferred embodiment of the process, the 2-chloro-3-oxopentanoic acid ester is produced with sulfuryl chloride and is used without purification in the raw form present after removing under vacuum the gaseous reaction products and distilling off excess sulfuryl chloride.

As the formamidinium salt, there is suitably used a formamidine salt with a strong inorganic acid, such as, hydrochloric acid or sulfuric acid, or a lower aliphatic carboxylic acid, such as, acetic acid. Preferred formamidinium salts are formamidinium chloride and formamidinium acetate. As the polar protic solvent, there is suitably used a lower alcohol, preferably the one corresponding to the 2-chloro-3-oxopentanoic acid ester used, thus especially preferably is ethanol or in particular methanol.

Any base that causes no undesired side reactions and is sufficiently soluble in the solvent used is suitable as the base. Preferably alkali alcoholates of lithium, sodium or potassium are used with lower alcohols, in particular those having 1 to 4 C atoms. Especially preferred are the sodium alcoholates, primarily the one derived in each case from the alcohol also used as a solvent. To suppress side reactions, it has turned out to be especially advantageous to dose the alkali alcoholate, according to the progress of the reaction, slowly into the given mixture of the 2-chloro-3-oxopentanoic acid ester with the formamidinium salt.

Another preferred embodiment of the reaction uses potassium carbonate as the base and methanol as the solvent. Here, the limited solubility of the potassium carbonate takes care of a low base concentration in the reaction mixture, so that the total amount of potassium carbonate can be added at one time and then it gradually dissolves.

The reaction between the 2-chloro-3-oxopentanoic acid ester and the formamidinium salt is advantageously performed at a relatively low temperature, preferably at 0° C. to 30° C.

Preferably, here a slightly excess amount of formamidinium salt is used, namely, 1.5 times the theoretically required amount. For 1 mole of 2-chloro-3-pentanoic acid ester, suitably 2 equivalents of base or preferably a slightly larger amount is used.

After the end of the reaction into 5-chloro-6-ethyl-4-hydroxypyrimidine, the latter can be isolated according to one of the usual or conventional methods, optionally purified, and then reacted with phosphoryl chloride in a way known in the art into the 4,5-dichloro-6-ethyl pyrimidine. In a preferred embodiment, the 4-hydroxy compound is not isolated, but the reaction mixture is first acidified, suitably by the introduction of gaseous hydrochloric acid, up to a clearly acidic reaction (pH between 3 and 6, optimally 5,). Then, preferably under reduced pressure, the solvent, suitably methanol or ethanol, is distilled off to a large extent. After adding a higher boiling, inert solvent, which acts as an entrainer, the remaining alcohol, as well as any optionally still-present water and/or acetic acid, is distilled off.

In this context, "inert" means only that the higher boiling solvent enters into no disruptive reactions with phosphoryl chloride during the final reaction. As the inert, higher-boiling solvents which are suitable, for example, alkylated aromatic hydrocarbons, such as, toluene, xylene or ethylbenzene, preferably toluene, are used.

Another use of the 5-chloro-6-ethyl-4-hydroxypyrimidine produced according to the invention consists in hydrogenolytically dehalogenating the latter as in known processes with hydrogen on a palladium catalyst. In this way, the 6-ethyl-4-hydroxypyrimidine is easily accessible while avoiding the drawbacks mentioned above.

The following examples clarify the embodiment of the invention.

EXAMPLE 1

5-Chloro-6-ethyl-4-hydroxyprimidine

To a solution of 8.6 g (0.049 mol) of 2-chloro-3-oxopentanoic acid methylester (content 94 percent) and 6.04 g (0.075 mol) of formamidinium chloride in 10 ml of methanol, there was added within 2 hours at 20° to 22° C., while stirring, 21.6 g of sodium methylate solution (30 percent in methanol, 0.12 mol). After another 3 hours of stirring, neutralization with conc. hydrochloric acid (pH about 5) and evaporation to dryness on the rotary evaporator were performed. The residue was taken up with 20 ml of water and extracted out three times with ethyl acetate. The combined organic phases were dried on sodium sulfate, the solvent was distilled off and the solid residue was dried at 50° C. and 100 torr. The following data concerns the product of this example:

| Yield: | | 7.42 g (93 percent) |
|---|---|---|
| Melting point: | | 144° to 145° C. |
| $^1$H-NMR: | $\delta =$ | 1.30 (t, 3H), 2.85 (q, 2H), |
| (CDCl$_3$, 300 MHz) | | 8.20 (s, 1H), 13.05 (br.s, 1H) |

EXAMPLE 2

A mixture of 5.0 g (0.030 mol) of 2-chloro-3-oxopentanoic acid methyl ester (content 98.6 percent), 3.14 g (0.039 mol) of formamidinium chloride, 9.1 g (0.066 mol) of potassium carbonate and 25 g of methanol was stirred at 10° C. for 5.5 hours. Then the mixture was acidified with conc. hydrochloric acid to about pH 5 and worked up as in Example 1. The yield of the product was 3.8 g (78 percent).

EXAMPLE 3

To a solution of 5.35 g (0.030 mol) of 2-chloro-3-oxopentanoic acid methyl ester (content 93.5 percent) and 2.93 g (0.036 mol) of formamidinium chloride in 5.1 g of ethanol there was added, within 3 hours at 10° C., 19.15 g of sodium ethylate solution (22.5 percent in ethanol, 0.063 mol) while stirring. The working up was performed as described in Example 1. The yield of the product was 4.74 g (95 percent).

EXAMPLE 4

To a solution of 5.35 g (0.030 mol) of 2-chloro-3-oxopentanoic acid methyl ester (content 93.5 percent) and 2.92 g (0.036 mol) of formamidinium chloride in 5.1 g of methanol there was dosed 3.08 g (0.030 mol) of triethylamine (as a 30 percent solution in methanol) within 4.5 hours at 10° C., while stirring. The working up was performed as described in Example 1. The yield of the product was 3.14 g (64 percent).

EXAMPLE 5

To a solution of 6.7 g (0.040 mol) of 2-chloro-3-oxopentanoic acid methyl ester (content 98 percent) and 4.79 g (0.046 mol) of formamidinium acetate in 5 g of methanol there was dosed within 30 minutes and at 12° C., while stirring, 14.4 g of sodium methylatesolution (30 percent in methanol, 0.08 mol). The working up was performed as described in Example 1. The yield of the product was 5.41 g (82 percent).

EXAMPLE 6

To a solution of 5.42 g (0.030 mol) of 2-chloro-3-oxopentanoic acid methyl ester (content 92.2 percent) and 3.75 g (0.018 mol) of formamidinium sulfate in 5 g of methanol there was added, within 30 minutes and at 10° C., while stirring, 11.4 g of sodium methylate solution (30 percent in methanol, 0.063 mol). The working up was performed as described in Example 1. The yield of the product was 2.06 g (42 percent).

EXAMPLE 7

4,5-dichloro-6-ethylpyrimidine

A mixture of 3.19 g (0.020 mol) of 5-chloro-4-ethyl-6-hydroxypyrimidine, 15.33 g (0.10 mol) of phosphoryl chloride and 45 g of toluene was heated to 100° C. and stirred at this temperature for 80 minutes. The excess phosphoryl chloride and the toluene were distilled off and the residue was mixed with 30 ml of dichloromethane and 20 ml of water. The mixture was refluxed after 30 minutes, extracted with 3×30 ml of dichloromethane and dried on sodium sulfate. The dichloromethane solution was evaporated and the residue was distilled at 125° C./12 torr in the bulb tube apparatus. The following data concerns the product of this example:

| Yield: | | 2.77 g (77 percent) |
|---|---|---|
| Boiling point: | | 89° to 94° C./12 torr |
| $^1$H-NMR | $\delta =$ | 1.36 (t, 3H), 3.00 (q, 2H) |
| (CDCl$_3$, 300 MHz) | | 8.79 (s, 1H) |

EXAMPLE 8

4,5-dichloro-6-ethylpyrimidine (one-pot process)

To 53.6 g (0.40 mol) of 3-oxopentanoic acid methyl ester there was added, at 12° C. and within 25 minutes, 56.8 g (0416 mol) of sulfuryl chloride while stirring. The gases produced (HCl, SO$_2$) were absorbed in water. Next the excess sulfuryl chloride, together with the remaining gaseous products, was removed in a vacuum and the residue was mixed with 56.2 g (0.54 mol) of formamidinium acetate and 50 g of methanol. At 12° to 16° C., 172 g of sodium methylate solution (30 percent in methanol, 0.96 mol) was added within 45 minutes. Stirring was performed for another 2.5 hours at 12° C. and then hydrochloric acid gas was introduced until a pH of about 2 was reached (about 20 minutes). At 90° C., first most of the methanol was distilled off, then 500 g of toluene was added and the temperature was slowly raised until only toluene still distilled over (overhead temperature about 114° C.). After cooling to 80° C., 291 g (1.89 mol) of phosphoryl chloride was added within 30 minutes, and the temperature increase was limited to less than 5 degrees. Next the mixture was stirred another 4.5 hours at 80° C., the excess phosphoryl chloride was distilled off with the toluene to a large extent and the viscous residue was diluted with toluene. The mixture thus obtained was cooled to 20° C. and mixed carefully with 400 ml of water so that the temperature did not rise above 40° C. The dark colored organic phase was separated, washed with sodium bicarbonate solution, dried on sodium sulfate and the toluene was distilled off. The residue (about 52 g) was fractionated in the water jet vacuum. The yield of the product was 46.4 g (65.5 percent relative to the 3-oxopentanoic acid methyl ester).

EXAMPLE 9

To 28.8 g (0.162 mol) of 2-chloro-3-oxopentanoic acid methyl ester (content 92.2 percent) and 22.5 g (0.21 mol) of formamidinium acetate in 20 g of methanol there was added, within 20 minutes and at 11° C., while stirring, 69 g of sodium methylate solution (30 percent in methanol, 0.38 mol). After another 3 hours of stirring at 11° C., 20 g (0.55 mol) of hydrochloric acid gas was introduced, and a pH of about 3 was reached. The methanol was distilled off under reduced pressure (40° C. to 45° C.; 250 torr), 180 ml of toluene was added and the remaining methanol as well as the water and acetic acid by-products were completely distilled off. The remaining mixture was brought to 80° C. and mixed with 115 g (0.75 mol) of phosphoryl chloride. After 4 hours of stirring at 80° C. to 90° C., the excess phosphoryl chloride was distilled off (42° C. to 45° C., 250 torr). The residue was diluted with 100 ml of toluene and then mixed slowly at 11° C. to 20° C. with 140 ml of water. The organic phase was separated, washed with 20 g each of saturated sodium bicarbonate solution and water and fractionated in a vacuum (23 torr). The yield of the product was 22.7 g (95 percent) (76 percent, relative to the 2-chloro-3-oxopentanoic acid methyl ester).

EXAMPLE 10

(Amounts Standardized to 1,000g of Product Yield)

1,148 g of sulfuryl chloride was instilled in 1,095 g of 3-oxopentanoic acid methyl ester at 12° C. while stirring, within 30 minutes. After another hour of reacting, the excess sulfuryl chloride was drawn off in a water jet vacuum, and the reaction mixture cooled to about 5° C. and then again warmed up gradually to about 10° C. Then a solution of 1,165 g of formamidinium acetate in 1,036 g of methanol was first added and then a solution of 1,071 g of sodium methylate in 2,500 g of methanol was instilled, and the temperature rose to 16° C. After about 2.5 hours, the reaction mixture was brought to an apparent pH of 3 by introducing about 800 g of HCl gas within about 30 minutes. In doing so the temperature rose to 21° C. Then, at 40° C. to 50° C. and 500 torr, the methanol was distilled off with most of the water and acetic acid by-products. After suitable heating with continuous addition of 4,520 g of toluene, the remaining methanol/water/acetic acid mixture was distilled off with the toluene azeotropically until no more acetic acid could be detected in the distillate. After cooling to 88° C., within 30 minutes a mixture of 6,037 g of phosphoryl chloride and 496 g of toluene was instilled. After 3 hours of reaction, the excess phosphoryl chloride was distilled off at 60° C. and a pressure of 200 torr, which was gradually lowered to 50 torr. The residue was diluted with 5,427 g of toluene, cooled to 20° C. and carefully mixed with 8.29 l of water. After 20 minutes of stirring, the aqueous phase was separated and the organic phase was washed once with 2,176 g of saturated sodium bicarbonate solution. The toluene was distilled off at 60° C. under reduced pressure, until a vacuum of 12 torr was reached. Finally, the residue was distilled at 12 torr (boiling range: 89° C. to 94° C.).

What is claimed is:

1. Process for the production of 4,5-dichloro-6-ethyl-pyrimidine:

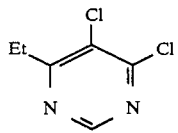

characterized in that a 2-chloro-3-oxopentanoic acid ester of the formula

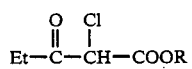

in which R is an alkyl group with 1 to 4 C atoms, is condensed with a formamidinium salt:

and X⁻ *is the anion of a strong inorganic acid or a lower aliphatic carboxylic acid, in the presence of a base in a polar, protic solvent into* 5-chloro-6-ethyl-4-hydroxypyrimidine:

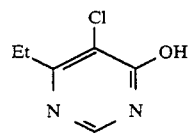

and the latter is reacted with phosphoryl chloride into the product (1).

2. Process according to claim 1 wherein an alkali alcoholate of general formula M O—R', in which M is lithium, sodium or potassium and R' is an alkyl group with 1 to 4 C atoms, is used as a base and the corresponding alcohol is used as a solvent.

3. Process according to claim 2 wherein sodium methylate or sodium ethylate is used as an alkali alcoholate.

4. Process according to claim 3 wherein the alkali alcoholate solution is slowly dosed into a given mixture that contains the 2-chloro-3-oxopentanoic acid ester and the formamidinium salt.

5. Process according to claim 2 wherein the alkali alcoholate solution is slowly dosed into a given mixture that contains the 2-chloro-3-oxopentanoic acid ester and the formamidinium salt.

6. Process according to claim 1 wherein potassium carbonate is used as a base and methanol is used as a solvent.

* * * * *